US009822382B2

(12) United States Patent
Kawai Shikishima

(10) Patent No.: US 9,822,382 B2
(45) Date of Patent: Nov. 21, 2017

(54) PROCESS FOR MAKING ETHANOL BY FERMENTATION

(71) Applicant: Evonik Degussa GmbH, Essen (DE)

(72) Inventor: Regina Tie Kawai Shikishima, Sao Paulo (BR)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/114,941

(22) PCT Filed: Jan. 20, 2015

(86) PCT No.: PCT/EP2015/050968
§ 371 (c)(1),
(2) Date: Jul. 28, 2016

(87) PCT Pub. No.: WO2015/113864
PCT Pub. Date: Aug. 6, 2015

(65) Prior Publication Data
US 2017/0002383 A1    Jan. 5, 2017

Related U.S. Application Data

(60) Provisional application No. 61/933,589, filed on Jan. 30, 2014.

(51) Int. Cl.
*C12P 7/06*    (2006.01)
(52) U.S. Cl.
CPC ............ *C12P 7/06* (2013.01); *C12P 2203/00* (2013.01); *Y02E 50/17* (2013.01)
(58) Field of Classification Search
None
See application file for complete search history.

(56) References Cited

U.S. PATENT DOCUMENTS

| 8,765,427 B2 * | 7/2014 | Murata ................ C12P 7/06 435/162 |
| 9,416,375 B2 * | 8/2016 | Fernholz ............... A01N 37/16 |
| 2009/0061490 A1 | 3/2009 | Edwards et al. |
| 2013/0344556 A1 | 12/2013 | Fernholz et al. |

FOREIGN PATENT DOCUMENTS

| WO | WO 02/03799 | 1/2002 |
| WO | WO 2009/026706 | 3/2009 |
| WO | WO 2011/116042 | 9/2011 |
| WO | WO 2011/139364 | 11/2011 |
| WO | WO 2012/027469 | 3/2012 |

OTHER PUBLICATIONS

Sanchez et al. (Bioresource Technol., vol. 99, 2008, pp. 5270-5295).*
International Search Report for corresponding international application PCT/EP2015/050968 filed Jan. 20, 2015.
Written Opinion of the International Searching Authority for corresponding international application PCT/EP2015/050968 filed Jan. 20, 2015.
International Preliminary Report on Patentability for corresponding international application PCT/EP2015/050968 filed Jan. 20, 2015.

* cited by examiner

*Primary Examiner* — Hope Robinson
(74) *Attorney, Agent, or Firm* — Law Office of: Michael A. Sanzo, LLC

(57) ABSTRACT

A process for making ethanol by fermentation comprises the steps fermenting a mash comprising a fermentable sugar with a yeast to form a fermented mash comprising ethanol, separating a yeast concentrate from the fermentation mash, adding a mineral acid to the yeast concentrate to provide an acidified yeast concentrate having a pH between 1.8 and 3.0, adding a peroxycarboxylic acid to the acidified yeast concentrate in an amount of from 5 to 80 ppm by weight to provide a treated yeast concentrate, and fermenting a mash comprising a fermentable sugar with addition of treated yeast concentrate to form a fermented mash comprising ethanol.

20 Claims, No Drawings

PROCESS FOR MAKING ETHANOL BY FERMENTATION

CROSS REFERENCE TO RELATED APPLICATIONS

The present application is U.S. national stage of international application PCT/EP2015/050968, which had an international filing date of Jan. 20, 2015, and which was published in English under PCT Article 21(2) on Aug. 6, 2015. The application claims the benefit of U.S. provisional application 61/933,589, filed on Jan. 30, 2014, the contents of which is incorporated by reference herein.

FIELD OF THE INVENTION

The present invention relates to a process for making ethanol by fermentation in which bacterial contamination can be controlled efficiently without use of antibiotics.

BACKGROUND OF THE INVENTION

Ethanol production by fermentation has become a major source of renewable fuel for transportation. Yeast fermentation of sugars derived from sugar cane, corn, sorghum or sugar beet feedstock and recovery of ethanol from the fermentation mash by distillation is used industrially for producing ethanol as gasoline additive or transportation fuel. Recovering yeast from the fermentation mash by centrifugation and recycle of recovered yeast to the fermentation can be used to increase fermentation rates and ethanol productivity. Byproducts from the fermentation, such as dried distillers grains and solubles (DDGS) from corn based fermentation or dried yeast from sugar cane based fermentation, are used as animal feed or feed additives.

A common problem in the production of fuel ethanol by fermentation is contamination of the fermentation mash with bacteria, in particular with lactic acid and acetic acid producing bacteria, which can lead to lowered ethanol yield and can interfere with yeast recycle by causing yeast flocculation. Antibiotics that act selectively on bacteria have been used to reduce bacterial contamination, but the use of such antibiotics is undesirable because it leads to contamination of fermentation byproducts with antibiotics and can lead to development of antibiotics resistance in bacteria.

An acid treatment lowering the pH to less than 2.5 is commonly applied to reduce bacterial contamination of recovered yeast before recycling it to fermentation. However, such an acid treatment is not sufficiently effective against acid tolerant bacteria, such as lactic acid and acetic acid producing bacteria.

WO 2011/116042 proposes to control growth of bacteria in an ethanol fermentation system by carrying out fermentation in the presence of a nonoxidizing biocide or a stabilized oxidizer, such as stabilized peracetic acid. The nonoxidizing biocide or stabilized oxidizer is added to the fermentation vessel.

WO 2012/027469 proposes to reduce bacteria levels in a fermentation system by introducing an organic oxidizing compound, such as peracetic acid, and an inorganic oxidizing compound, such as hydrogen peroxide, into a fermentation mash.

US 2009/0061490 discloses fermenting xylose in a clarified sugar hydrolysate, where a yeast slurry is separated from the fermentation broth, treated with an oxidant to reduce microbial contaminants and re-introduced into the fermentation. Treatment with the oxidant is carried out in the pH range between 3 and 6.

SUMMARY OF THE INVENTION

The inventor of the present invention has found that surprisingly a peroxycarboxylic acid is much more effective in reducing bacterial contamination without affecting yeast fermentation activity in an ethanol fermentation process using yeast recovery and recycling when the peroxycarboxylic acid is added to an acidified recovered yeast before the recovered yeast is reused for fermentation as compared to adding the peroxycarboxylic acid directly to the fermentation mash or to a recovered yeast that has not been acidified.

The present invention therefore provides a process for making ethanol by fermentation comprising the steps a) fermenting a mash comprising a fermentable sugar with a yeast to form a fermented mash comprising ethanol, b) separating a yeast concentrate from the fermented mash obtained in step a), c) adding a mineral acid to the yeast concentrate obtained in step b) to provide an acidified yeast concentrate having a pH between 1.8 and 3.0, d) adding a peroxycarboxylic acid to the acidified yeast concentrate in an amount of from 5 to 80 ppm by weight to provide a treated yeast concentrate, and e) fermenting a mash comprising a fermentable sugar with addition of treated yeast concentrate obtained in step d) to form a fermented mash comprising ethanol.

DETAILED DESCRIPTION OF THE INVENTION

The process of the invention comprises a step a) of fermenting a mash with a yeast, with the mash comprising a fermentable sugar.

Suitable fermentable sugars are monosaccharides, such as glucose, fructose or galactose, and disaccharides, such as sucrose, maltose or lactose. The mash may be derived from plants containing fermentable sugars, such as sugar cane, sugar beets or sweet sorghum. Alternatively, the mash may be derived from plants containing starch, such as corn, potatoes, wheat or rice, or from plants containing cellulose by hydrolysis, preferably by enzymatic hydrolysis, of starch or cellulose. Preferably, the mash is sugar cane juice, sugar cane molasses or a combination of both.

The mash is fermented with a yeast, preferably *saccharomyces cerevisiae*, to form a fermented mash comprising ethanol. Fermentation step a) may be carried out as batch fermentation, fed-batch fermentation, continuous fermentation or semi-continuous fermentation. In batch fermentation, all of the mash and the yeast are added to a fermenter and are fermented until the yeast has converted the fermentable sugars to ethanol to the desired degree. In fed-batch fermentation, a yeast suspension, optionally containing a part of the mash, is charged to a fermenter and mash is fed to the fermenter over a period of time during which the yeast converts a major part of the fermentable sugars to ethanol. After the feeding of mash is stopped, fermentation is continued for a further time period to complete conversion of fermentable sugars to ethanol before the fermenter is discharged. In continuous fermentation, yeast and mash are fed continuously to a fermenter and a corresponding amount of fermented mash is withdrawn continuously to maintain the amount of material inside the fermenter essentially constant. In semi-continuous fermentation, yeast and mash are fed continuously, but fermented mash is withdrawn from the fermenter at intervals. Fermentation step a) is preferably carried out as batch fermentation or fed-batch fermentation. Fermentation is preferably carried out in a mixed fermenter and the temperature in the fermenter is preferably maintained in the range of from 28 to 37° C.

In a subsequent step b), a yeast concentrate is separated from the fermented mash obtained in step a). Separation may be carried out with any method known to be suitable for separating yeast from an aqueous alcoholic suspension. Separation is preferably carried out by decantation or centrifugation, most preferably by centrifugation. Centrifugation is preferably carried out with a decanting centrifuge or a disk separator, most preferably with a disk separator. Separation is preferably carried out to obtain a yeast suspension containing 60 to 80% by weight yeast cells, often referred to as yeast cream, which is then diluted with water to provide a yeast concentrate. After dilution the yeast concentrate preferably contains 25 to 35% by weight yeast cells.

In step c) of the process of the invention, a mineral acid is added to the yeast concentrate obtained in step b) to provide an acidified yeast concentrate having a pH between 1.8 and 3.0. Preferably, sulfuric acid is used as the mineral acid. Addition of mineral acid can be carried out in batch or continuously. Continuous addition of mineral acid is preferably carried out in a continuous stirred tank reactor. Addition is preferably carried out with pH control using a pH sensor, preferably using a glass pH electrode. Addition of mineral acid is preferably carried out at a temperature of from 25 to 37° C.

In step d) of the process of the invention, a peroxycarboxylic acid is added to the acidified yeast concentrate. The peroxycarboxylic acid is preferably a peroxymonocarboxylic acid which preferably has from 1 to 8 carbon atoms and is most preferably peroxyacetic acid. The peroxycarboxylic acid is added to the acidified yeast concentrate in an amount of from 5 to 80 ppm by weight.

Step d) can be carried out subsequent to step c) either in batch or continuously. Subsequent continuous addition of a peroxycarboxylic acid is preferably carried out using two continuous stirred tank reactors in series with mineral acid addition to the first reactor and peroxycarboxylic acid addition to the second reactor. In an alternative and preferred embodiment, steps c) and d) are carried out in parallel by adding mineral acid and peroxycarboxylic acid to the same continuous stirred tank reactor and adjusting the amount of added mineral acid to maintain a pH between 1.8 and 3.0 in the continuous stirred tank reactor.

The peroxycarboxylic acid can be added intermittently or continuously. If the peroxycarboxylic acid is added intermittently, the addition can be on a regular schedule with predetermined intervals of addition and periods of addition. Alternatively, the addition can be on an as needed basis depending on the level of bacterial contamination in the fermented mash or the yeast concentrate. When the peroxycarboxylic acid is added intermittently, it is preferably added in an amount of from 20 to 80 ppm, more preferably from 30 to 80 ppm. When intermittent addition is done at a regular schedule, the intervals of addition are preferably chosen to be from 8 to 200 hours and the periods of addition of peroxycarboxylic acid are preferably chosen to be from 10 to 120 minutes if step d) is carried out in batch and from 8 to 150 hours if step d) is carried out continuously. When the peroxycarboxylic acid is added continuously, it is preferably added in an amount of from 5 to 30 ppm, more preferably from 10 to 20 ppm.

The peroxycarboxylic acid is preferably used in combination with hydrogen peroxide at a molar ratio of peroxycarboxylic acid to hydrogen peroxide of from 0.02:1 to 5:1, preferably of from 0.1:1 to 2.5:1. When peroxyacetic acid is used as the peroxycarboxylic acid, it is preferably used in the form of an equilibrium peroxyacetic acid. The term equilibrium peroxyacetic acid refers to a mixture comprising peroxyacetic acid, acetic acid, hydrogen peroxide and water in chemical equilibrium. Most preferably, an equilibrium peroxyacetic acid comprising from 3 to 17% by weight peroxyacetic acid is used.

In a further step e) a mash comprising a fermentable sugar is fermented with addition of treated yeast concentrate obtained in step d) to form a fermented mash comprising ethanol. The mash fermented in step e) may be the same mash as in step a) or may differ from the mash of step a) in the amount of fermentable sugars or in the source of the mash. The process conditions for fermenting in step e) may be the same as in step a) or they may be different. Preferably, both steps a) and e) are carried out as batch or as fed-batch fermentations. More preferably, steps a) and e) are carried out with the same mash at essentially the same process conditions, i.e. the treated yeast concentrate obtained in step d) is reused in a fermentation carried out the same way as the fermentation from which the yeast has been separated in step b). Most preferably, the sequence of steps b) to e) is repeated several times with step e) of a sequence constituting step a) of the subsequent sequence, giving an overall process of repeated fermenting with yeast recycle through steps b) to e).

Steps d) and e) of the process are preferably carried out to provide an average time between adding a peroxycarboxylic acid to the acidified yeast concentrate in step d) and addition of treated yeast concentrate in step e) of at least 10 minutes. Preferably, the average time is from 10 minutes to 5 hours, more preferably from 0.5 to 5 hours. For a continuous processing of yeast concentrate, where step d) is carried out in a continuous stirred tank reactor, the average time refers to the average residence time of yeast concentrate in the reactor, calculated as the ratio of the average liquid volume inside the reactor to the volume flow rate of yeast concentrate into the reactor.

In a first preferred embodiment of the process of the invention, fermentation is carried out in batch in several fermenters operated in parallel and fermenters are discharged in succession to provide an essentially constant flow of fermented mash to step b) of separating a yeast concentrate. Yeast is preferably separated with a continuously operated centrifuge and yeast cream from the centrifuge is transferred to a stirred tank reactor where it is diluted with water to a yeast concentrate containing 25 to 35% by weight yeast cells. Sulfuric acid is fed to the same stirred tank reactor to adjust the pH to a value between 1.8 and 3.0. Thereafter, an equilibrium peroxyacetic acid is fed, in an amount of from 20 to 80 ppm peroxyacetic acid based on the amount of yeast concentrate. The treated yeast concentrate is fed the fermenters after a treatment time of from 1 to 4 hours.

In a second preferred embodiment of the process of the invention, fermentation is carried out in fed-batch in several fermenters operated in parallel and fermenters are discharged in succession to provide an essentially constant flow of fermented mash to step b) of separating a yeast concentrate. Yeast is preferably separated with a continuously operated centrifuge and yeast cream from the centrifuge is transferred to a first continuous stirred tank reactor where it is diluted with water to a yeast concentrate containing 25 to 35% by weight yeast cells. The yeast concentrate is fed to a second continuous stirred tank reactor, to which sulfuric acid and an equilibrium peroxyacetic acid are fed, regulating the feed of sulfuric acid to maintain a pH between 1.8 and 3.0. Equilibrium peroxyacetic acid is fed continuously or intermittently and the feed of equilibrium peroxyacetic acid is adjusted to add from 5 to 30 ppm peroxyacetic acid continuously or from 20 to 80 ppm peroxyacetic acid intermittently, each based on the amount of fed yeast concentrate. The treated yeast concentrate is passed to a buffer vessel from which it is fed the fermenters before fed-batch fermentation is started. The volume of the continuous stirred tank reactor and the buffer vessel are chosen to provide an average time between adding peroxyacetic acid to the acidified yeast concentrate and transfer of treated yeast concentrate to a fermenter of from 1 to 4 hours.

The process of the invention provides a high and stable ethanol productivity, because it allows maintaining a high recycle of yeast and prevents problems arising from bacterial contamination of the fermentation, such as lowered ethanol yield or flocculation of yeast in the fermented mash which interferes with yeast separation. Bacterial contamination is lowered and controlled without contaminating yeast or fermented mash with antibiotics or persistent biocides and without a risk of inducing antibiotics resistance in bacteria.

EXAMPLES

Bacterial and yeast cell counts, yeast cell viability and yeast flocculation were determined as described in A. J. Oliveira et al., Curso de treinamento em microbiologia, Piracicaba: FERMENTEC and ESALQ, 1996 and in A. J. Oliveira et al., Métodos para o controle microbiológico na produção de açúcar e álcool, Piracicaba: FERMENTEC, FEALQ and ESALQ, 1996. Bacterial infection rates were calculated as the ratio of the rod bacteria cell count and the yeast cell count.

Examples 1 (Comparative) and 2

The examples were carried out with a yeast cream obtained by separating yeast from a fermented sugar cane mush from a sugar cane ethanol production mill operating with batch fermentation and yeast recycle. The yeast cream was diluted with water to a yeast cell content of about 24% by weight and the pH of the diluted yeast cream was adjusted to a value of 1.8 by adding sulfuric acid.

In example 1, the acidified diluted yeast cream was kept at 30° C. for 2 hours before it was analyzed microbiologically.

Then 322 ml of acidified diluted yeast cream were placed in a vessel and 678 ml of cane must having a pH of 6.2 were added with mixing in 5 portions with 1 h intervals between additions. Fermentation of the cane must with the acidified diluted yeast cream was carried out at 33° C. for 21 h. The final pH of the fermented mash was 4.8.

In example 2, equilibrium peroxyacetic acid PERACLEAN® 15 of Evonik was added to the acidified diluted yeast cream in an amount of 50 mg/l and the resulting treated yeast concentrate was kept at 30° C. for 1.7 hours before it was analyzed microbiologically. Thereafter, fermentation was carried out as in example 1.

Bacterial and yeast cell counts, infection rates and yeast cell viabilities determined for the treated yeast concentrate before fermentation and the fermented mash after 21 h are summarized in tables 1 and 2. The data show that treatment of the yeast concentrate with peroxyacetic acid at pH 1.8 before using it for the fermentation is effective in preventing bacterial contamination of the fermented mash and does not affect yeast viability in the fermentation.

TABLE 1

Example 1, bacterial contamination without peroxyacetic acid

|  | Treated yeast concentrate | Fermented mash |
|---|---|---|
| Rod bacteria cells/ml | $11*10^6$ | $61*10^6$ |
| Yeast cells/ml | $490*10^6$ | $220*10^6$ |
| Infection rate in % | 2.2 | 28 |
| Yeast viability in % | 78 | 77 |

TABLE 2

Example 2, bacterial contamination with addition of 50 ppm peroxyacetic acid

|  | Treated yeast concentrate | Fermented mash |
|---|---|---|
| Rod bacteria cells/ml | $2.9*10^6$ | $6.1*10^6$ |
| Yeast cells/ml | $550*10^6$ | $230*10^6$ |
| Infection rate in % | 0.5 | 2.6 |
| Yeast viability in % | 73 | 81 |

Examples 3 (Comparative) and 4

Examples 1 and 2 were repeated without adding peroxyacetic acid in example 3 and with addition of equilibrium peroxyacetic acid PERACLEAN® 15 in an amount of 60 mg/l peroxyacetic acid in example 4. The treated yeast cream was kept at 30° C. for 2 hours before it was analyzed microbiologically and fermentation was started. The cane must used in the fermentation had a pH of 5.7. The fermented mash was analyzed microbiologically after 19 h and had a pH of 3.9 at this time.

Bacterial and yeast cell counts, infection rates and yeast cell viabilities determined for the treated yeast concentrate before fermentation and the fermented mash after 19 h are summarized in tables 3 and 4.

TABLE 3

Example 3, bacterial contamination without peroxyacetic acid

|  | Treated yeast concentrate | Fermented mash |
|---|---|---|
| Rod bacteria cells/ml | $24*10^6$ | $23*10^6$ |
| Yeast cells/ml | $630*10^6$ | $220*10^6$ |
| Infection rate in % | 3.8 | 10.5 |
| Yeast viability in % | 80 | 79 |

TABLE 4

Example 4, bacterial contamination with addition of 60 ppm peroxyacetic acid

|  | Treated yeast concentrate | Fermented mash |
|---|---|---|
| Rod bacteria cells/ml | $1.8*10^6$ | $0.22*10^6$ |
| Yeast cells/ml | $710*10^6$ | $180*10^6$ |

TABLE 4-continued

Example 4, bacterial contamination with addition
of 60 ppm peroxyacetic acid

|  | Treated yeast concentrate | Fermented mash |
|---|---|---|
| Infection rate in % | 0.3 | 0.1 |
| Yeast viability in % | 83 | 80 |

Examples 5, 6, 7 (All Comparative) and 8

The examples were carried out with a yeast cream obtained by separating yeast from a fermented sugar cane mush from a sugar cane ethanol production mill that operates with fed-batch fermentation and yeast recycle. The yeast cream was diluted with water to a yeast cell content of about 27% by weight. The pH of the diluted yeast cream was 4.0.

In example 5, the diluted yeast cream was kept at 30° C. for 3.6 hours before it was analyzed microbiologically.

In example 6, equilibrium peroxyacetic acid PERACLEAN® 15 of Evonik was added to the diluted yeast cream in an amount of 50 mg/l and the resulting treated yeast concentrate was kept at 30° C. for 2.3 hours before it was analyzed microbiologically.

In example 7, the pH of the diluted yeast cream was adjusted to a value of 2.0 by adding sulfuric acid and the resulting acidified yeast concentrate was kept at 30° C. for 2.5 hours before it was analyzed microbiologically.

In example 8, the pH of the diluted yeast cream was adjusted as in example 7, equilibrium peroxyacetic acid PERACLEAN® 15 of Evonik was added to the acidified diluted yeast cream in an amount of 50 mg/l and the resulting treated yeast concentrate was kept at 30° C. for 2.0 hours before it was analyzed microbiologically.

Bacterial and yeast cell counts, infection rates, yeast cell viabilities and pH determined for the treated yeast concentrate after the times sated above are summarized in table 5. The data of table 5 show that treatment of the yeast concentrate with peroxyacetic acid is ineffective when the pH has not been adjusted to the claimed range by addition of acid. There is a synergistic effect between adjusting the pH of the yeast concentrate by adding mineral acid and adding the peroxyacetic acid.

TABLE 5

Examples 5 to 8, bacterial contamination with and without
pH adjustment and with and without peroxyacetic acid
addition

| Example | 5 | 6 | 7 | 8 |
|---|---|---|---|---|
| Added peroxyacetic acid in mg/l | 0 | 50 | 0 | 50 |
| pH of treated yeast concentrate | 4.26 | 4.17 | 2.30 | 2.40 |
| Rod bacteria cells/ml | 60*10$^6$ | 68*10$^6$ | 95*10$^6$ | 14*10$^6$ |
| Yeast cells/ml | 930*10$^6$ | 820*10$^6$ | 690*10$^6$ | 830*10$^6$ |
| Infection rate in % | 6.5 | 8.3 | 14 | 1.7 |
| Yeast viability in % | 92 | 86 | 89 | 88 |

Examples 9 to 11

Examples 9 to 11 were carried out in a sugar cane ethanol production mill operating 6 fermenters in fed-batch. The fermented mash is sent to a centrifuge which separates yeast cream with an average yeast content of 63% by weight. The yeast cream is diluted with water to an average yeast content of 27% by weight and transferred to a stirred yeast cream recovery tank. Diluted yeast cream is passed continuously from this tank to a stirred yeast treatment tank at a rate of from 42 to 127 m$^3$/h. Sulfuric acid is added to the yeast treatment tank to maintain a pH in the range from 1.8 to 2.8. The average residence time in both the yeast cream recovery tank and the yeast treatment tank is in the range of from 1.3 to 4.0 h. Fermentation is carried out by charging the acidified yeast concentrate to a fermenter over a 1 to 2 h period, followed by feeding sugar cane mash with a sugar content of 22° Brix and a pH of 5.8 to the fermenter over a 6 h period. Fermentation is continued for a further 2 h without feed and the fermented mash is sent to a centrifuge. Bacterial contamination was monitored by microbiological analysis of samples of fermented mash taken before feeding the mash to a centrifuge. Samples were analyzed for bacterial and yeast cell counts and for yeast cell viability and yeast flocculation.

In example 9, equilibrium peroxyacetic acid PERACLEAN® 15 of Evonik was dosed to the yeast treatment tank for 28 h in an amount of 60 ppm during days 3 and 4 of the experiment. pH in the yeast treatment tank was maintained in the range of from 1.84 to 2.02. Results for bacterial contamination in fermenters 2 and 4 are given in tables 6 and 7. The data demonstrate that bacterial contamination and yeast flocculation are reduced upon addition of peroxyacetic acid and return when addition of peroxyacetic acid is stopped.

TABLE 6

Example 9, bacterial contamination in fermenter 2

| Day | Rod bacteria cells/ml | Infection rate in % | Yeast viability in % | Yeast flocculation in % | Average fermentation efficiency in % |
|---|---|---|---|---|---|
| 1 | 106*10$^6$ | 41 | 87 | 30 | 87.9 |
| 3 | 28*10$^6$ | 11 | 79 | 53 | 90.1 |
| 4 | 39*10$^6$ | 10 | 80 | 5 | 90.0 |
| 5 | 51*10$^6$ | 18 | 82 | 58 | 88.2 |

TABLE 7

Example 9, bacterial contamination in fermenter 4

| Day | Rod bacteria cells/ml | Infection rate in % | Yeast viability in % | Yeast flocculation in % | Average fermentation efficiency in % |
|---|---|---|---|---|---|
| 2 | 141*10$^6$ | 49 | 88 | 60 | 90.2 |
| 3 | 53*10$^6$ | 11 | 85 | 63 | 90.1 |
| 4 | 20*10$^6$ | 3 | 80 | 0 | 90.0 |
| 6 | 57*10$^6$ | 22 | 83 | 55 | 89.6 |

In example 10, equilibrium peroxyacetic acid PERACLEAN® 15 of Evonik was dosed to the yeast treatment tank for 43 h during days 6 and 7 of the experiment in an amount that was lowered stepwise from 49 ppm to 20 ppm. pH in the yeast treatment tank was maintained in the range of from 1.97 to 2.60. Results for bacterial contamination in fermenters 2 and 3 are given in tables 8 and 9. The data demonstrate that continuous addition of 20 ppm peroxyacetic acid to the acidified yeast concentrate is sufficient to control bacterial contamination and avoid yeast flocculation.

TABLE 8

Example 10, bacterial contamination in fermenter 2

| Day | Rod bacteria cells/ml | Infection rate in % | Yeast viability in % | Yeast flocculation in % | Average fermentation efficiency in % |
|---|---|---|---|---|---|
| 1 | $32*10^6$ | 15 | 77 | 58 | 91.0 |
| 4 | $16*10^6$ | 5.8 | 80 | 0 | 90.9 |
| 6 | $9.6*10^6$ | 2.8 | 81 | 0 | 91.4 |
| 7 | $1.4*10^6$ | 0.5 | 75 | 0 | 90.4 |
| 8 | $24*10^6$ | 8.1 | 79 | 0 | 90.3 |
| 9 | $29*10^6$ | 11 | 79 | 37 | 90.1 |

TABLE 9

Example 10, bacterial contamination in fermenter 3

| Day | Rod bacteria cells/ml | Infection rate in % | Yeast viability in % | Yeast flocculation in % | Average fermentation efficiency in % |
|---|---|---|---|---|---|
| 1 | $43*10^6$ | 19 | 86 | 48 | 91.0 |
| 5 | $23*10^6$ | 6.3 | 80 | 0 | 91.4 |
| 6 | $3.0*10^6$ | 1.5 | 73 | 0 | 91.4 |
| 7 | $0.7*10^6$ | 0.2 | 70 | 0 | 90.4 |
| 8 | $13*10^6$ | 4.4 | 78 | 0 | 90.3 |
| 9 | $22*10^6$ | 7.5 | 84 | 45 | 90.1 |

In example 11, equilibrium peroxyacetic acid PERACLEAN® 15 of Evonik was dosed to the yeast cream recovery tank on days 2 and 3 of the experiment for 13 h in an amount of 50 ppm, followed by dosing for 28 h in an amount of 30 ppm. During this period the pH in the yeast cream recovery tank was in the range of from 3.0 to 3.3. Then dosing of peroxyacetic acid to the yeast cream recovery tank was stopped and peroxyacetic acid was dosed to the yeast treatment tank for 18 h in an amount of 30 ppm. During this period the pH in the yeast treatment tank was about 2.0. Results for bacterial contamination in fermenters 3 and 6 are given in tables 10 and 11. The data demonstrate that addition of peroxyacetic acid is effective only for an acidified yeast concentrate at a pH of less than 3.0.

TABLE 10

Example 11, bacterial contamination in fermenter 3

| Day | Rod bacteria cells/ml | Infection rate in % | Yeast viability in % | Yeast flocculation in % | Average fermentation efficiency in % |
|---|---|---|---|---|---|
| 1 | $32*10^6$ | 10 | 77 | 40 | 90.2 |
| 2 | $32*10^6$ | 11 | 82 | 38 | 90.8 |
| 4 | $8.4*10^6$ | 2 | 76 | 0 | 90.1 |
| 6 | $24*10^6$ | 18 | 73 | 66 | 91.4 |

TABLE 11

Example 11, bacterial contamination in fermenter 6

| Day | Rod bacteria cells/ml | Infection rate in % | Yeast viability in % | Yeast flocculation in % | Average fermentation efficiency in % |
|---|---|---|---|---|---|
| 1 | $16*10^6$ | 6 | 80 | 0 | 90.2 |
| 2 | $23*10^6$ | 5 | 83 | 0 | 90.8 |
| 3 | $14*10^6$ | 5 | 89 | 0 | 91.0 |
| 5 | $25*10^6$ | 10 | 73 | 65 | 88.6 |

The invention claimed is:

1. A process for making ethanol by fermentation, with yeast recovery and recycling, comprising the steps:
    a) fermenting a mash comprising a fermentable sugar with a yeast to form a fermented mash comprising ethanol,
    b) separating a yeast concentrate from the fermentation mash obtained in step a),
    c) adding a mineral acid to the yeast concentrate obtained in step b) to provide an acidified yeast concentrate having a pH between 1.8 and 3.0,
    d) adding a peroxycarboxylic acid to the acidified yeast concentrate in an amount of from 5 to 80 ppm by weight to provide a treated yeast concentrate, and
    e) fermenting a mash comprising a fermentable sugar with addition of the treated yeast concentrate obtained in step d) to form a fermented mash comprising ethanol.

2. The process of claim 1, wherein in step b) a yeast suspension containing 60 to 80% by weight yeast cells is separated by centrifugation and said yeast suspension is diluted with water to provide said yeast concentrate.

3. The process of claim 1, wherein the peroxycarboxylic acid is peroxyacetic acid.

4. The process of claim 1, wherein the peroxycarboxylic acid is added intermittently in an amount of from 20 to 80 ppm by weight.

5. The process of claim 1, wherein the peroxycarboxylic acid is added continuously in an amount of from 5 to 30 ppm by weight.

6. The process of claim 1, wherein the peroxycarboxylic acid is used in combination with hydrogen peroxide at a molar ratio of peroxycarboxylic acid to hydrogen peroxide of from 0.02:1 to 5:1.

7. The process of claim 1, wherein the mash comprising a fermentable sugar is selected from the group consisting of: sugar cane juice, sugar cane molasses and a combination of both.

8. The process of claim 1, wherein the average time between adding a peroxycarboxylic acid to the acidified yeast concentrate in step d) and addition of treated yeast concentrate in step e) is at least 10 min.

9. The process of claim 1, wherein steps a) and e) are carried out as batch fermentations or as fed-batch fermentations.

10. The process of claim 2, wherein the peroxycarboxylic acid is peroxyacetic acid.

11. The process of claim 10, wherein the peroxyacetic acid is added intermittently in an amount of from 20 to 80 ppm by weight.

12. The process of claim 11, wherein the average time between adding a peroxycarboxylic acid to the acidified yeast concentrate in step d) and addition of treated yeast concentrate in step e) is at least 10 min.

13. The process of claim 12, wherein steps a) and e) are carried out as batch fermentations or as fed-batch fermentations.

14. The process of claim 10, wherein the peroxyacetic acid is added continuously in an amount of from 5 to 30 ppm by weight.

15. The process of claim 14, wherein the average time between adding a peroxycarboxylic acid to the acidified yeast concentrate in step d) and addition of treated yeast concentrate in step e) is at least 10 min.

16. The process of claim 15, wherein steps a) and e) are carried out as batch fermentations or as fed-batch fermentations.

17. A process for making ethanol by fermentation, with yeast recovery and recycling, comprising the steps:
   a) fermenting a mash comprising a fermentable sugar with a yeast in batch to form a fermented mash comprising ethanol, operating fermenters in parallel and discharging fermenters in succession to provide an essentially constant flow of fermented mash;
   b) separating a yeast cream from the fermentation mash obtained in step a) by centrifugation and diluting said yeast dream with water to provide a yeast concentrate containing 25 to 35% by weight yeast cells;
   c) adding a mineral acid to the yeast concentrate obtained in step b) to provide an acidified yeast concentrate having a pH between 1.8 and 3.0;
   d) adding an equilibrium peroxyacetic acid to the acidified yeast concentrate in an amount of from 20 to 80 ppm by weight to provide a treated yeast concentrate; and
   e) fermenting a mash comprising a fermentable sugar with addition of treated yeast concentrate obtained in step d) to form a fermented mash comprising ethanol;
   wherein the average time between adding peroxyacetic acid in step d) and adding the treated yeast concentrate obtained in step e) is from 1 to 4 hours.

18. The process of claim 17, wherein steps c) and d) are carried out in a continuous stirred tank reactor, to which sulfuric acid and the equilibrium peroxyacetic acid are fed.

19. A process for making ethanol by fermentation, with yeast recovery and recycling, comprising the steps:
   a) fermenting a mash comprising a fermentable sugar with a yeast in fed-batch to form a fermented mash comprising ethanol, operating fermenters in parallel and discharging fermenters in succession to provide an essentially constant flow of fermented mash;
   b) separating a yeast cream from the fermentation mash obtained in step a) by centrifugation and diluting said yeast dream with water to provide a yeast concentrate containing 25 to 35% by weight yeast cells;
   c) adding a mineral acid to the yeast concentrate obtained in step b) to provide an acidified yeast concentrate having a pH between 1.8 and 3.0;
   d) adding an equilibrium peroxyacetic acid to the acidified yeast concentrate in an amount of from 5 to 80 ppm by weight to provide a treated yeast concentrate; and
   e) fermenting a mash comprising a fermentable sugar in fed-batch with addition of treated yeast concentrate obtained in step d) before fed-batch fermentation is started to form a fermented mash comprising ethanol;
   wherein the average time between adding peroxyacetic acid in step d) and adding the treated yeast concentrate obtained in step e) is from 1 to 4 hours.

20. The process of claim 19, wherein steps c) and d) are carried out in a continuous stirred tank reactor, to which sulfuric acid and the equilibrium peroxyacetic acid are fed.

* * * * *